United States Patent [19]

Hahn et al.

[11] Plant 5,151

[45] Dec. 6, 1983

[54] GRAPEVINE

[75] Inventors: Luther C. Hahn, Thermal; Joseph Maranto, Bakersfield, both of Calif.

[73] Assignee: Superior Farming Company, Bakersfield, Calif.

[21] Appl. No.: 338,372

[22] Filed: Jan. 11, 1982

[51] Int. Cl.[3] ..... A01H 5/03

[52] U.S. Cl. ..... Plt./47

[58] Field of Search ..... Plt./47

*Primary Examiner*—Robert E. Bagwill

*Attorney, Agent, or Firm*—Harris, Kern, Wallen & Tinsley

[57] ABSTRACT

A very large, vigorous productive grapevine, having a slender trunk and very long split straps, reddish brown bark, medium to long cane and round, slightly enlarged nodes and shoots basically green with reddish longitudinal striations and tips growing straight up, bifurcated and trifurcated tendrils, medium size bud, slightly pointed, medium size leaves with U shaped petiolar sinus; date of bloom and fruit ripening 7–10 days earlier than Superior Seedless (U.S. Plant Pat. No. 3,106) and 14 days earlier than Thompson Seedless (unpatented), clusters of medium size, loose to compact, seedless white colored berries irregular in size, mostly large, firm, crisp, attractive, sweet taste, attributable to an early high solids-sugar and low acid content.

1 Drawing Figure

ORIGIN OF THE VARIETY

The present variety of grapevine was discovered during the 1978 growing season in a vineyard on Rancho Primero, located south of Coachella, Riverside County, Calif. The description of the characteristics was made during the 1979 and 1980 growing seasons. The grapevine was discovered as a sport of Superior Seedless (U.S. Plant Pat. No. 3,106). In the spring, the present variety of grapevine manifested an earlier bud break and shoot growth than the surrounding Superior Seedless grapevines. Throughout the season, the sport vine, which closely resembles the Superior Seedless variety, maintained the advanced growth and period of cluster ripening. The present variety has distinctive new growth habits which class it as a special table grape. The Superior Seedless variety is a cross between the Cardinal and an unnamed seedless sport (unpatented) with a complex parentage. The appearance of the present variety indicates an expression in the generation manifestation of a dominant character gene previously unnoticed in the Superior Seedless variety.

ASEXUAL REPRODUCTION OF THE VARIETY

In 1979, the present variety was selected for asexual reproduction in preparation for developing a commercial vineyard planting.

The variety was successfully propagated by green whip grafting, and T budding methods on several young Superior Seedless and mature Thompson Seedless grapevines grown on two ranches owned by Superior Farming Company approximately 300 miles to the north of Coachella, in Bakersfield, Kern County, Calif. In addition, several thousand young vines were also propagated by using a green tip cutting technique in a greenhouse in Tucson, Ariz., which is also owned by Superior Farming Company.

In 1980, the first crop of grapevines of the variety propagated by grafting and budding in the Bakersfield area, was harvested and the vines bore true to the original seedless sport mother vine in all respects.

SUMMARY OF THE VARIETY

A very large, vigorous productive grapevine, having a slender trunk and very long split straps, reddish brown bark, medium to long cane and round, slightly enlarged nodes and shoots basically green with reddish longitudinal striations and tips growing straight up, bifurcated and trifurcated tendrils, medium size bud, slightly pointed, medium size leaves with U shaped petiolar sinus; date of bloom and fruit ripening 7–10 days earlier than Superior Seedless (U.S. Plant Pat. No. 3,106) and 14 days earlier than Thompson Seedless (unpatented), clusters of medium size, loose to compact, seedless white colored berries irregular in size, mostly large, firm, crisp, attractive, sweet taste, attributable to an early high solids-sugar and low acid content.

BRIEF DESCRIPTION OF THE DRAWING

The drawing is an illustration, by photographic reproduction, of leaves, cane and cluster of berries of the variety.

DESCRIPTION OF THE VARIETY

The external appearance and other botanical characteristics of this new and distinctive variety of grapevine are as follows:

Vine:

*Size.*—Very large — bushy appearance.

*Vigor.*—Very vigorous.

*Productive capacity.*—Productive — Tendency to produce a small second crop of small clusters on current season's growth.

*Trunk.*—Slender, very long split straps.

*Color of bark.*—Brown gray, reddish brown (under bark).

*Canes.*—Thickness — medium length — medium long 4″–12″. Width at node $\frac{1}{2}$″–$\frac{3}{4}$″.

*Nodes.*—Round, slightly enlarged. Length — medium, average distance 4″–6″.

*Shoots.*—Length — medium to long, circular to slightly flat. (This variety shoot lengths 3″–14″, Superior Seedless 1"-3", Rancho Primero, Coachella, Mar. 7, 1979.) Shoot number — 20 with some primary laterals. Color — basically green with reddish longitudinal striations, mostly at the tip end. Shoot contour — smooth.

*Tendrils.*—Location — subcontinuous. Length 4"-9". Thickness — Medium. Color — green with reddish at the base. Form — Bifurcated and trifurcated. Texture — smooth. Buds — Shape — slightly pointed. Size — medium. Bud fruitfulness — basal mostly unfruitful, medium and distal end mostly fruitful, seldom dead.

Leaves:

*Size.*—Medium.

*Density.*—Heavy.

*Length.*—(Mature Leaf) 4"-6". Color — (upper surface) green, (lower surface) — light pale green.

*Texture.*—Glabrous. Petiole — Length 3"-4", slightly flat. Sinus — Form (petiole sinus) — U shaped, occasionally overlapping, (later sinus) — shallow.

*Leaf margin.*—Teeth (dentation) average — 10 points per lobe. Total teeth 50-60. Teeth size — Irregular. Teeth shape — pointed — serrate. Leaf surface — smooth. Thick-medium. Five lobed.

Inflorescence: Number borne per cane, 4-6; Number borne per vine, 30-35 (6 canes); Inflorescence size — Medium.

Flowers:

*Bloom (Coachella Valley).*—Date of first bloom — Apr. 8, 1979. Full bloom — April 12. Last bloom — April 17. On April 18, the variety had some visible berry set (Superior Seedless, none).

*Size.*—Medium. Color of pistil — green.

*Stamens.*—Number — 5. Amount of pollen — abundant. Pollen shape — ovoid (oval).

*Size of pollen.*—22 microns.

Fruit:

*Ripening period.*—Very early, about 7-10 days ahead of Superior Seedless, 14 days ahead of Thompson Seedless, and almost at the same time as the Perlette grape variety. Rancho Primero, May 29, 1979 — solids-sugar (refractometer test) 13.0° B, acid 0.74° (Superior Seedless on same date, solids-sugar 7.6° B, acid 2.66°). Rancho Primero, June 7, 1979 — solids-sugar 16.0° B, acid 0.54° (Superior Seedless on same date, solids-sugar 12.0° B, acid 1.26°). Bakersfield area, June 20, 1980 — solids-sugar 14.0° B (Superior Seedless on same date, solids-sugar 5.0° B). Bakersfield area, June 27, 1980 — solids-sugar 14.8° B, acid 1.06°, sugar/acid ratio 14.0, juice pH 3.2 (Superior Seedless on same date, solids-sugar 10.0° B, acid 1.74°, sugar/acid ratio 5.74, juice pH 2.8). Rancho Primero, Ranch 44, June 10, 1981 — solids-sugar 17.0° B (Superior Seedless on same date 14.6° B); Bakersfield area, Ranch 209, June 26, 1981 — solids-sugar 17.0° B (Superior Seedless on same date 13.2° B). Bakersfield area, Ranch 51, June 26, 1981 — solids-sugar 14.0° B (Superior Seedless on same date 12.2° B).

*Cluster.*—Size — Medium. Weight — Average one pound. Compactness — Loose to compact. Form — Cylindrical to conical.

*Berry.*—Size — Mostly large. Uniformity of berry size — Variable. Dimensions — Longitudinal axis — 12-24 mm. Number of berries per cluster — 125 average. Form — Ellipsoidal to ovoid (oval). Skin — Thick. Taste — Sweet. Texture — Very firm-crisp. Color — Light green. Tendency to crack — None. Capstem (pedicel) — Strong. Seeds — None (occasionally a seed trace). Juice color — colorless. Pulp — adheres to skin, greenish white. Flavor — Mild. Eating quality — Good.

Use: Dessert.

Resistance to adverse weather conditions: Resistant to cold, drought, heat, wind, and soil conditions.

Storage and shipping quality: Untested.

The results of electrophoresis analysis, which is used as a criteria for positive identification of varieties and which also provides a genetic makeup to supplement morphological data, confirms the difference between the present variety and the Superior Seedless and Thompson Seedless varieties. In the analysis of the enzymatic comparisons with Superior Seedless and Thompson Seedless, the present variety shows a definite difference in the banding patterns of the anodal esterase (EST) and catechol oxidase (CO). These are not present in the Superior Seedless variety. In addition, in similar comparisons with Thompson Seedless, the present variety shows a definite difference in the banding patterns of indolphenol oxidase (IPO), alcohol dehydrogenase (ADH), and leucine aminopeptidase (LAP). The complete results of the electrophoresis analysis are set out below:

Acid Phosphatase (HP):

| | rF .33 | rF .36 |
|---|---|---|
| Thompson Seedless | − | + |
| Superior Seedless | + | + |
| Present Variety | + | + |

Esterase (EST):

| | Catodal (mm) 11* | Catodal (mm) 16 | rF .63 | rF .90 |
|---|---|---|---|---|
| Thompson Seedless | − | − | − | − |
| Superior Seedless | + | + | − | − |
| Present variety | + | + | + | + |

Catechol Oxidase (CO):

| | rF .19 | rF .24 | rF .30 | rF .36 | rF .40 | rF .46 |
|---|---|---|---|---|---|---|
| Thompson Seedless | − | + | + | + | − | − |
| Superior Seedless | + | + | + | + | + | + |
| Present Variety | + | + | + | + | − | + |

Indolphenol Oxidase (IPO):

| | rF .54 | rF .66 |
|---|---|---|
| Thompson Seedless | − | + |
| Superior Seedless | + | − |
| Present Variety | + | − |

Alcohol Dehydrogenase (ADH):

| | rF .31 | rF .46 |
|---|---|---|
| Thompson Seedless | − | + |
| Superior Seedless | + | + |
| Present Variety | + | + |

Catalase (CAT):

| | rF .07 |
|---|---|
| Thompson Seedless | + |
| Superior Seedless | + |

-continued

| | | | |
|---|---|---|---|
| Present Variety | | + | |
| Glutamate-Oxalacetate Transaminase (GOT): | | | |
| | rF | | |
| | .29 | .36 | .45* |
| Thompson Seedless | + | + | + |
| Superior Seedless | + | + | + |
| Present Variety | + | + | + |
| Peroxidase (PER): | | | |
| | Cathodal | rF | |
| | 23 mm | .40 | .71 |
| Thompson Seedless | + | + | + |
| Superior Seedless | + | + | + |
| Present Variety | + | + | + |
| Leucine Aminopeptidase (LAP): | | | |
| | rF | | |
| | .55 | .64 | |
| Thompson Seedless | + | – | |
| Superior Seedless | – | + | |
| Present Variety | – | + | |
| Malic Enzyme (ME): | | | |
| | rF | | |
| | .21 | | |
| Thompson Seedless | + | | |
| Superior Seedless | + | | |
| Present Variety | + | | |
| Malate Dehydrogenase (MDH): | | | |
| | rF | | |
| | .49 | | |
| Thompson Seedless | + | | |
| Superior Seedless | + | | |
| Present Variety | + | | |

*very faint

The appearance of growth habit, period of fruit ripening and the genetic makeup, indicates that the present variety is the result of a natural change in the gene, and the early growth and ripening expression is of significant economic importance.

The present variety also proved that even at different climatic and soil conditions of Riverside and Kern Counties, Calif., under which the variety is grown, it does not revert to the original Superior Seedless growth pattern and date of ripening expression. The variety maintains the same novel early characteristics of growth in the Bakersfield area, Central Valley of California.

The grapevine and its fruit herein described may vary in slight detail due to climatic and soil conditions under which the variety may be grown, the present description being of the variety as grown in the Coachella and Southern San Joaquin Valleys.

The cultivar name for the instant variety is Sugrafive.

We claim:

1. A new and distinct variety of grapevine, substantially as illustrated and described, which is characterized by a very large, vigorous productive vine, having a slender trunk and very long split straps, reddish brown bark, medium to long cane and round, slightly enlarged nodes and shoots basically green with reddish longitudinal striations and tips growing straight up, bifurcated and trifurcated tendrils, medium size bud, slightly pointed, medium size leaves with U shaped petiolar sinus; date of bloom and fruit ripening 7–10 days earlier than Superior Seedless (U.S. Plant Pat. No. 3,106) and 14 days earlier than Thompson Seedless (unpatented); clusters of medium size, loose to compact, seedless white colored berries irregular in size, mostly large, firm, crisp, attractive, sweet taste, attributable to an early high solids-sugar and low acid content.

* * * * *

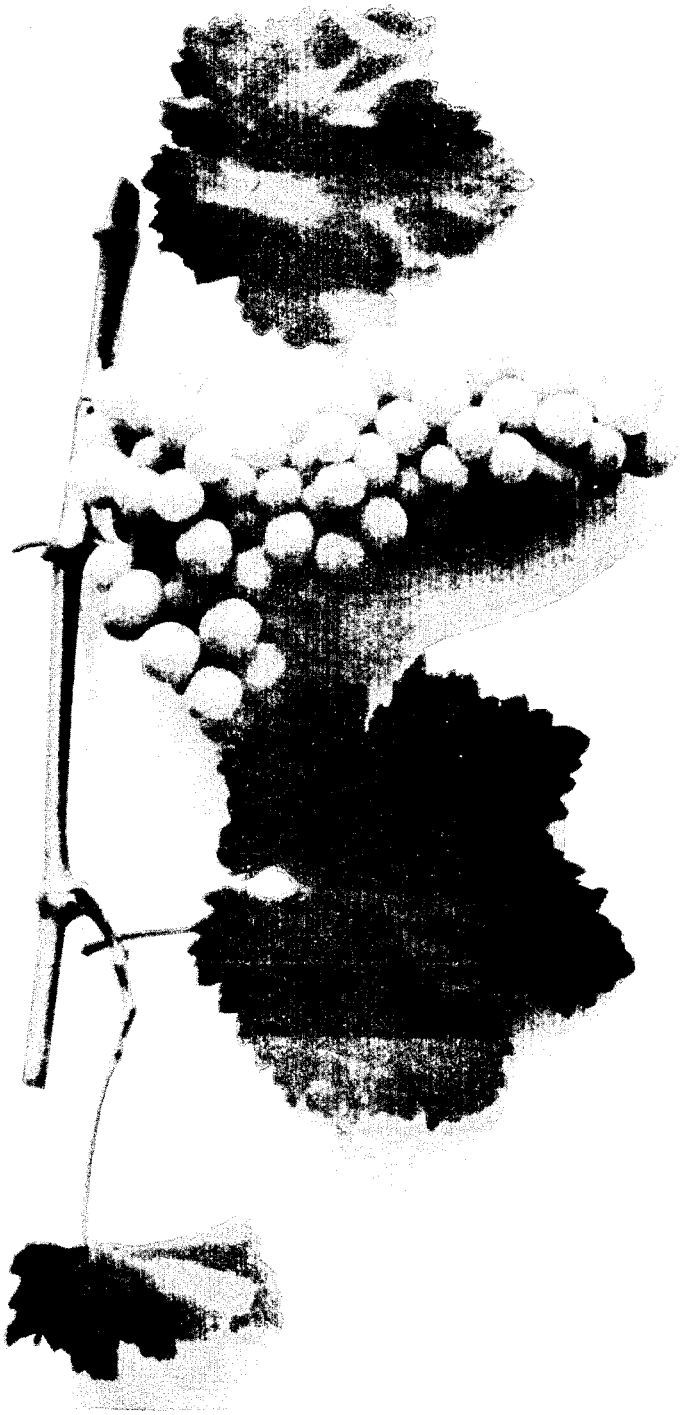

UNITED STATES PATENT AND TRADEMARK OFFICE

CERTIFICATE OF CORRECTION

PATENT NO. : PP 5151

DATED : December 6, 1983

INVENTOR(S) : Luther C. Hahn and Joseph Maranto

It is certified that error appears in the above-identified patent and that said Letters Patent is hereby corrected as shown below:

The title of the invention should read:

GRAPEVINE cv. SUGRAFIVE

Signed and Sealed this

Nineteenth Day of April, 1988

*Attest:*

DONALD J. QUIGG

*Attesting Officer*

*Commissioner of Patents and Trademarks*